(12) United States Patent
MacGregor

(10) Patent No.: US 11,111,195 B2
(45) Date of Patent: Sep. 7, 2021

(54) BIO-METHANOL PRODUCTION

(71) Applicant: Ultra Clean Ecolene Inc., Kincardine (CA)

(72) Inventor: Norman J. MacGregor, Kincardine (CA)

(73) Assignee: Ultra Clean Ecolene Inc., Kincardine (CA)

( * ) Notice: Subject to any disclaimer, the term of this patent is extended or adjusted under 35 U.S.C. 154(b) by 0 days.

(21) Appl. No.: 16/651,401

(22) PCT Filed: Sep. 21, 2018

(86) PCT No.: PCT/CA2018/051187
§ 371 (c)(1),
(2) Date: Mar. 27, 2020

(87) PCT Pub. No.: WO2019/060988
PCT Pub. Date: Apr. 4, 2019

(65) Prior Publication Data
US 2020/0283362 A1 Sep. 10, 2020

(30) Foreign Application Priority Data

Sep. 28, 2017 (CA) .............................. CA 2980573

(51) Int. Cl.
*C07C 29/151* (2006.01)
*C05F 17/50* (2020.01)
(Continued)

(52) U.S. Cl.
CPC ............ *C07C 29/1518* (2013.01); *C01B 3/36* (2013.01); *C02F 11/04* (2013.01); *C05F 17/50* (2020.01);
(Continued)

(58) Field of Classification Search
CPC ....... C07C 29/1518; C07C 31/04; C01B 3/36; C01B 2203/025; C01B 2203/061;
(Continued)

(56) References Cited

U.S. PATENT DOCUMENTS 8,188,322 B2   5/2012   Shaw
2008/0220489 A1   9/2008   Offerman
(Continued)

FOREIGN PATENT DOCUMENTS

CA   2135122 A1   5/1995
CA   2469653 A1   6/2003
(Continued)

OTHER PUBLICATIONS

Ajayi, Olusegun A. et al., Methanol Production from Cow Dung, Journal of Environmental and Earth Science, vol. 2, No. 7, 2012, pp. 9-16.
(Continued)

*Primary Examiner* — Jafar F Parsa
(74) *Attorney, Agent, or Firm* — Dorton & Willis, LLP

(57) ABSTRACT

Methods and systems for producing bio-methanol can include anaerobic digestion of a biomass feedstock to produce biogas including methane and carbon dioxide, partial oxidation of the biogas with oxygen from water electrolysis to produce syngas, synthesizing bio-methanol from the syngas and hydrogen from the water electrolysis, storing the bio-methanol, intermittently using battery based electricity to power the electrolysis during peak electricity demand, and intermittently using renewable electricity from another source during off-peak demand. Electricity can also optionally be obtained by periodically combusting a portion of the bio-methanol. The techniques provide a route for the production of bio-methanol without the engagement of fossil fuels as feedstocks and mitigating fossil fuel derived green-
(Continued)

house gas emissions from processing and utilization of transportation fuels and commercial or industrial alcohols.

20 Claims, 12 Drawing Sheets

(51) Int. Cl.
*C01B 3/36* (2006.01)
*C02F 11/04* (2006.01)
*C12M 1/107* (2006.01)
*C12M 1/00* (2006.01)
*C12P 5/02* (2006.01)
*C25B 1/04* (2021.01)
*C25B 15/02* (2021.01)

(52) U.S. Cl.
CPC ............ *C12M 21/04* (2013.01); *C12M 43/08* (2013.01); *C12P 5/023* (2013.01); *C25B 1/04* (2013.01); *C25B 15/02* (2013.01); *C01B 2203/025* (2013.01); *C01B 2203/061* (2013.01)

(58) Field of Classification Search
CPC . C05F 17/50; C02F 11/04; C25B 1/04; C25B 15/02
See application file for complete search history.

(56) References Cited

U.S. PATENT DOCUMENTS

| | | | |
|---|---|---|---|
| 2010/0114395 A1 | 5/2010 | Hinatsu et al. | |
| 2013/0210937 A1 | 8/2013 | Gonzalez | |
| 2013/0214542 A1* | 8/2013 | Knop | C25B 15/00 290/1 R |
| 2015/0240716 A1* | 8/2015 | Dietrich | C10L 3/10 60/780 |
| 2016/0053387 A1* | 2/2016 | Kutchcoskie | C25B 15/08 205/637 |
| 2019/0337876 A1* | 11/2019 | Short | C07C 29/1518 |

FOREIGN PATENT DOCUMENTS

| | | |
|---|---|---|
| CA | 2703715 A1 | 4/2009 |
| CA | 2972841 A1 | 10/2017 |
| WO | 03051803 A1 | 6/2003 |
| WO | 2016179476 A1 | 11/2016 |

OTHER PUBLICATIONS

Cantrell, Keri B. et al., Livestock waste-to-bioenergy generation opportunities, Bioresource Technology 99 (2008), pp. 7941-7953.
Shamsul, N.S. et al., An overview on the production of bio-methanol as potential renewable energy, Renewable and Sustainable Energy Reviews 33 (2014), pp. 578-588.
Surendra, K.C. et al., Anaerobic Digestion-Based Biorefinery for Bioenergy and Biobased Products, Industrial Biotechnology, vol. 11, No. 2, Apr. 2015, pp. 103-112.
Rao, P. Venkateswara et al., Biogas generation potential by anaerobic digestion for sustainable energy development in India, Renewable and Sustainable Energy Reviews 14 (2010), pp. 2086-2094.
European Patent Office; Search Report and Written Opinion in related International Patent Application No. PCT/CA2018/051187 dated Dec. 18, 2018; 7 pages.

* cited by examiner

BIO-METHANOL PRODUCTION

TECHNICAL FIELD

The technical field generally relates to the production of bio-methanol, and particularly to processes and systems for producing bio-methanol from naturally occurring elements.

BACKGROUND

Liquid biofuel can be produced from a variety of feedstocks and using various different processing technologies. Energy and reactant requirements for conventional liquid biofuel production techniques can lead to technical and economic challenges as well as elevated fossil fuel emissions.

SUMMARY

The techniques described herein relate to a route for the production of a liquid biofuel without the engagement of fossil fuels as feedstocks or fossil fuel sourced emissions, and more particularly to integrated processes and systems for producing a liquid hydrocarbon-based sustainable bio-methanol. The techniques enable mitigating fossil fuel derived greenhouse gas emissions from processing and utilization of transportation fuels and commercial or industrial alcohols. In some implementations, an electrolysis unit that is part of a bio-methanol production process is powered using different sources of energy at different electricity demand periods.

Various systems and processes described herein and recited in the claims reflect aspects and implementations of the invention.

DETAILED DESCRIPTION

Various techniques are described herein for bio-methanol production. In some implementations, systems and processes are provided for the production of bio-methanol (which may be referred to here as ECOLENE®). The bio-methanol can be dedicated as a liquid transportation biofuel, as a commercial/industrial alcohol, and/or as a liquid biofuel for generating greenhouse gas neutral electricity particularly during peak electrical demand periods. The bio-methanol can also be dedicated as a liquid storage medium for surplus and low-demand nuclear and/or renewable electricity as well as a novel medium for temporary storage of captured greenhouse gases from decomposed biomass for delayed release back to the atmosphere for balancing via photosynthesis.

One or more batteries can be implemented for powering electrolysis, where the battery unit can be charged during off-peak electricity demand and then used to power electrolysis during peak electricity demand. The battery-based methodology can also be integrated with the periodic use of bio-methanol as fuel for a generator that generates electricity for powering electrolysis. The electrolysis unit, which may include one or more electrolysis devices, can therefore be configured to receive power from multiple sources, notably from an AC source (e.g., grid) during off-peak periods, and from one or more batteries and/or one or more generators during peak periods. The power input from the different power sources can be modulated based on lower cost or higher availability of the electric power, or various other methods based on factors such as accumulated inventory (e.g., of bio-methanol), battery charge level, power demand for electrolysis, overall greenhouse gas emissions or life cycle analyses, and so on.

Described herein is thus an integrated technology that can activate a transition from emitting greenhouse gases, exhausted from fossil fuel combustion and decomposing biomass, to synthesize a liquid hydrocarbon (bio-methanol), while storing variable quantities of intermittently available surplus and low demand (off-peak) alternating current (AC) electricity in direct current (DC) storage batteries, while facilitating the provision of a steady state of DC to electrolyze water for the production of hydrogen and oxygen used to synthesize methanol, engaging only intermittently idled electricity generation and waste biomass. A portion of the surplus and low demand AC based power stored in DC batteries, while enabling a steady state production of hydrogen and oxygen from water, may be converted back to AC to serve variable periods of high demand (peak) electricity.

In addition, DC storage of surplus system-based AC enables DC battery banks to be incrementally expanded to serve this dual purpose in the transitioning of electricity supply to renewables, together with harmonizing system electricity supply and demand.

Figure 1A:
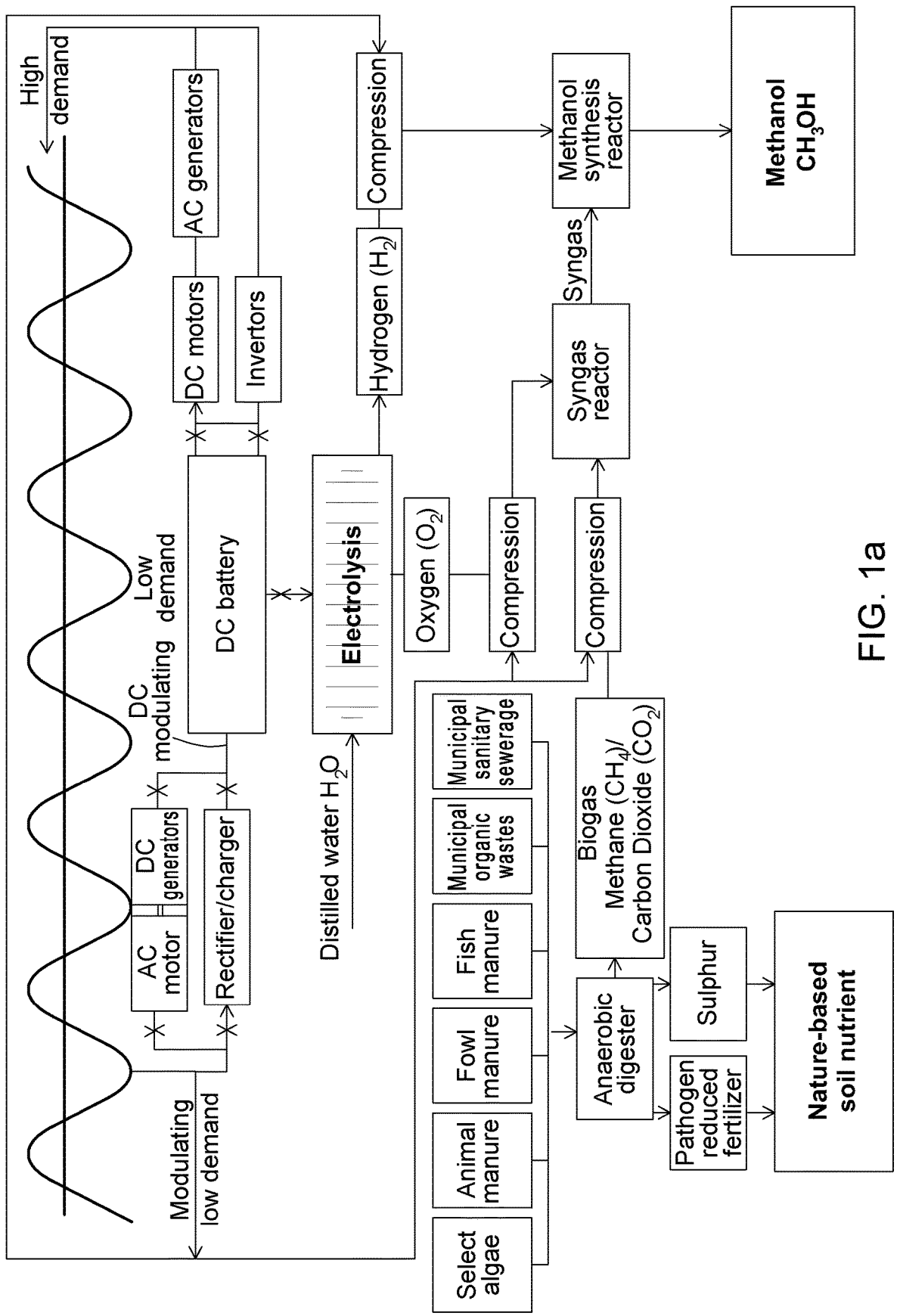
FIG. 1a is a block diagram of an integrated bio-methanol production process with greenhouse gas neutrality.
Figure 1B:
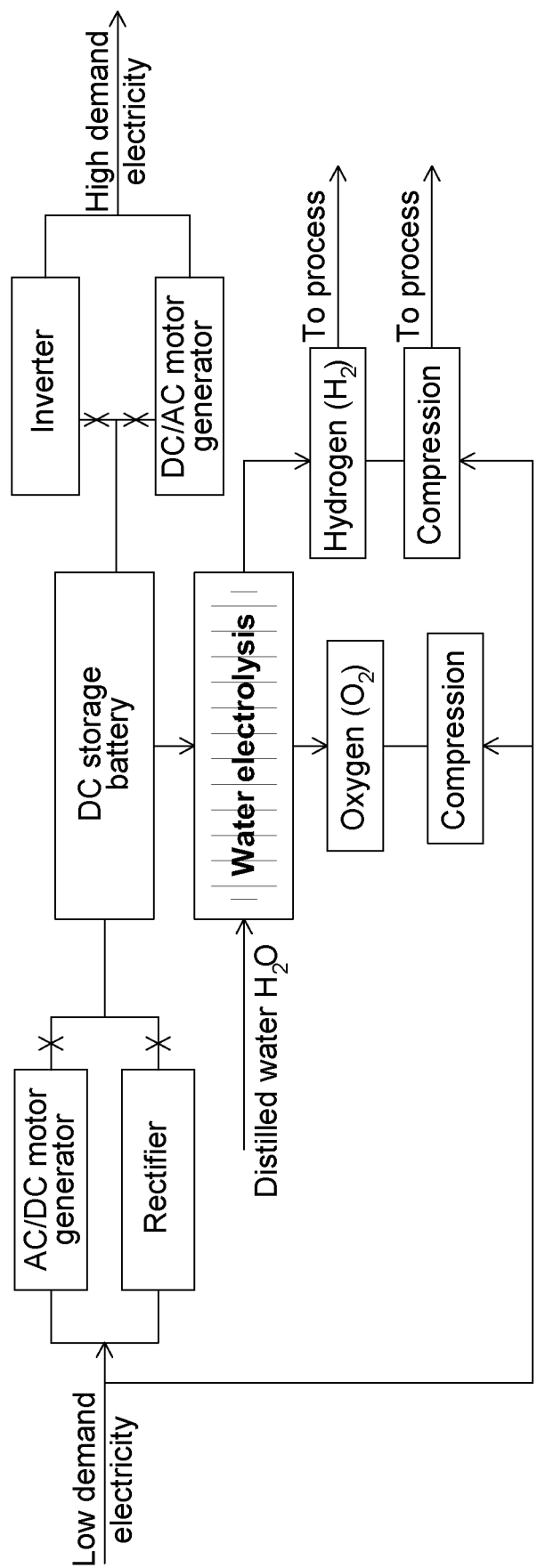
FIG. 1b is a block diagram of part of a bio-methanol production process.
Figure 1C:
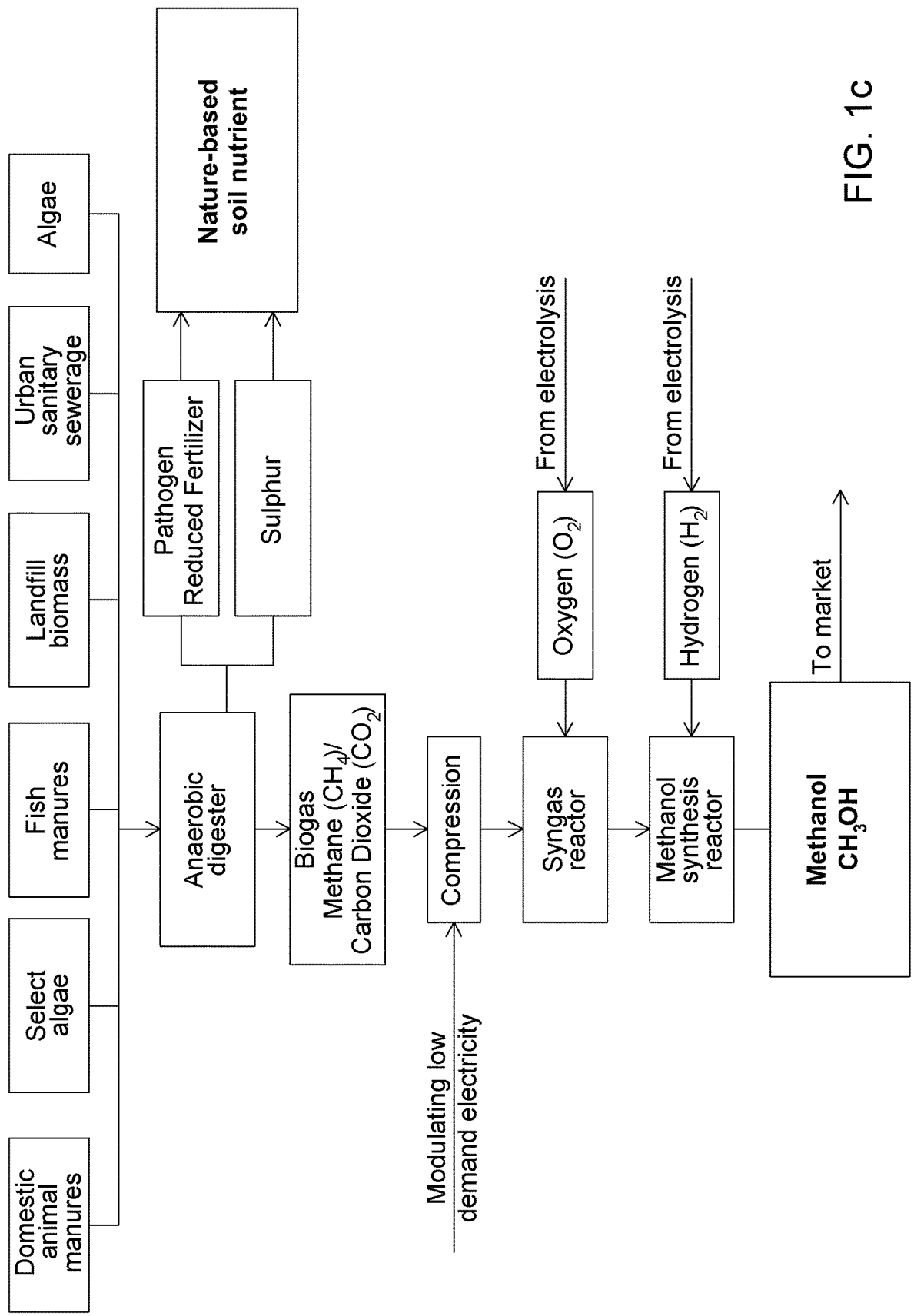
FIG. 1c is a block diagram of part of a bio-methanol production process.
Figure 1D:
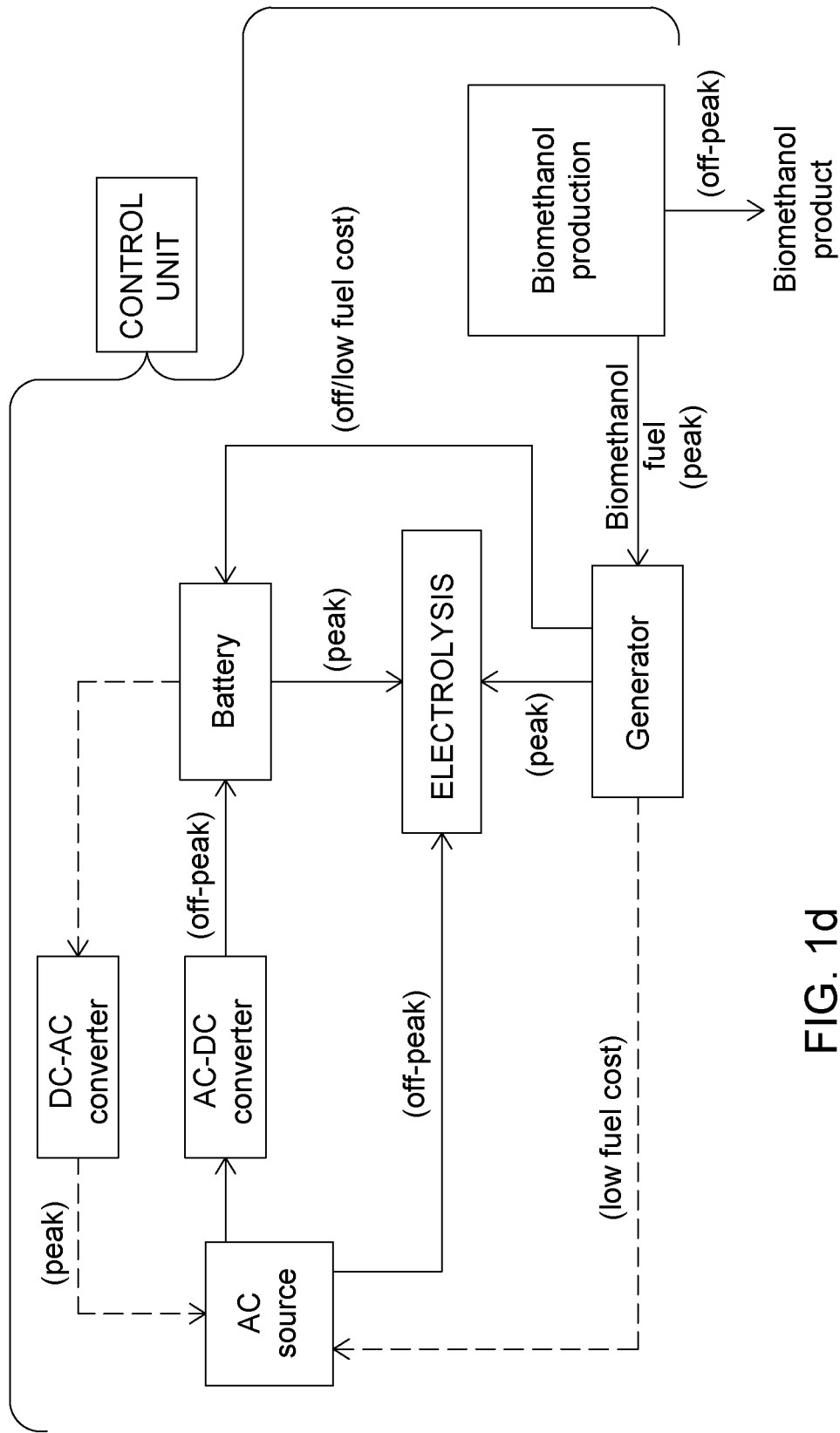
FIG. 1d is a block diagram of part of a bio-methanol production process showing power sources possibly used during peak and off-peak periods.

FIG. 1d schematically illustrates an example system in which different power sources are used for electrolysis at peak and off-peak periods. FIGS. 1a and 1b illustrate example systems in which a DC battery is used to power electrolysis.

In some implementations, a portion of grid-sourced modulating off-peak Alternating Current (AC) electricity is converted to Direct Current (DC), using AC-DC convertor (e.g., rectifiers and/or AC motor-driven DC generators), in variable amounts during intermittent periods of reduced electricity system demand, to charge and/or recharge expandable banks of DC batteries. In addition, a portion of the AC electricity is stored as DC, to operate water electrolysis equipment to produce gaseous hydrogen ($H_2$) and gaseous oxygen ($O_2$), simultaneously or independently, while operationally using a portion of the DC supply to operate DC-AC convertors (e.g., invertors and/or DC motor-driven AC generators), to produce system-based electricity during modulating periods of high electricity system demand.

The integrated process can facilitate introduction of a novel technology to incrementally transition the genesis of synthesizing a climate change benign hydrocarbon in the form of bio-methanol, to harmoniously replace petroleum-based fuels. The process can leverage multiple power sources and thus provide reliable and feasible operations for bio-methanol production, while enabling flexible use of different power sources in different proportions over time.

The adverse consequences of climate change are motivating the automotive industry to transition the use of petroleum to electricity, which creates the desire for storing intermittently available periods of surplus low-demand electricity and releasing stored energy to provide intermittent periods of high demand electricity. There may be many ways to store surplus electricity during low demand and return stored electricity during high demand including:

- pumping water uphill during low demand and operating hydro electric turbine generators with falling water during high demand;
- compressing air during surplus and low demand periods and releasing the compressed air to operate air turbine-driven generators during high demand periods;
- electrolyzing water to produce hydrogen and oxygen gases during low electricity demand and engaging fuel cells and/or combustion turbine generators to produce electricity during high demand;
- torquing mechanical energy during low electricity demand and relieving torqued energy to mechanically rotate electricity generators during high demand;
- charging Direct Current (DC) batteries during low demand and converting DC back to Alternating Current (AC), returning stored electron energy to the system during high demand.

In addition, incorporating water electrolysis while charging batteries and compressing gases for interim storage during low electricity demand is reflected on FIG. 1b.

In some implementations, there can be more or less a steady state drawdown on the storage batteries commensurate with the water electrolysis steady state demand. In some implementations, there can be a variable and intermittent drawdown when DC energy is required to produce AC back into the system during high demand, although this conversion from DC back into AC is optional. The DC storage can be variable in accordance with battery energy drawdown and the stored DC can serve as stand-by power for a methanol synthesis process, particularly an electrolysis step, although alternatively for other units for production of a biofuel in general.

The adverse consequences of climate change are also motivating the agricultural industry and urban communities to utilize urban organic wastes (e.g., from landfills), together with sanitary sewerage and all forms of domestic animal, fowl and aquaculture manures to be collectively digested without access to air, to produce, contain and utilize massive volumes of biogas which would otherwise blend with fossil fuel emissions into the atmosphere. Presently, biomass, which decomposes into biogas, consisting primarily of methane ($CH_4$) and carbon dioxide ($CO_2$) is burned in combustion turbine generators to generate electricity and/or to supplement natural gas distribution. However, biogas is a lower quality combustion fuel since the $CO_2$ content in biogas acts as an extinguisher reducing the heat rate and is passed into the atmosphere as greenhouse gas emissions. Anaerobic digestion of rural and urban biomass to produce, contain and utilize naturally occurring methane ($CH_4$) and carbon dioxide ($CO_2$) when used to integrate with sustainable hydrogen ($H_2$) and oxygen ($O_2$) in a steady state or batch process is reflected on FIG. 1c.

The incorporation of batteries for powering electrolysis provides a number of advantages. For example, by incorporating DC batteries for storing variable amounts of intermittently available surplus and low demand grid-sourced AC, expandable battery banks may be used to power water electrolysis for the steady state production of hydrogen and oxygen which can reduce or eliminate the need for certain electrolysis plant redundancies. Reliable electrolysis operation in addition to flexible power sourcing are facilitated. By enabling renewable/sustainable biomass to generate a regular supply of biogas, together with a steady state supply of hydrogen and oxygen from electrolysis, the processing of a sustainable liquid bio-hydrocarbon (e.g., bio-methanol) can be advantageously synthesized as a sustainable substitute for petroleum products.

Referring to FIGS. 2 to 14, the overall system and certain process variants will be described that include a battery and an optional bio-methanol fueled generator. It should be noted that various figures that illustrate the battery-based option, for instance FIG. 2 and others, should be understood as being schematic illustrations that do not necessarily show all of the equipment or components that could be used in implementations of the system. For example, such figures may not explicitly illustrate AC-DC or DC-AC converters or other components shown in FIG. 1a for instance, but such components may be included where required as part of any of the example systems illustrated and/or described herein.

Figure 2:
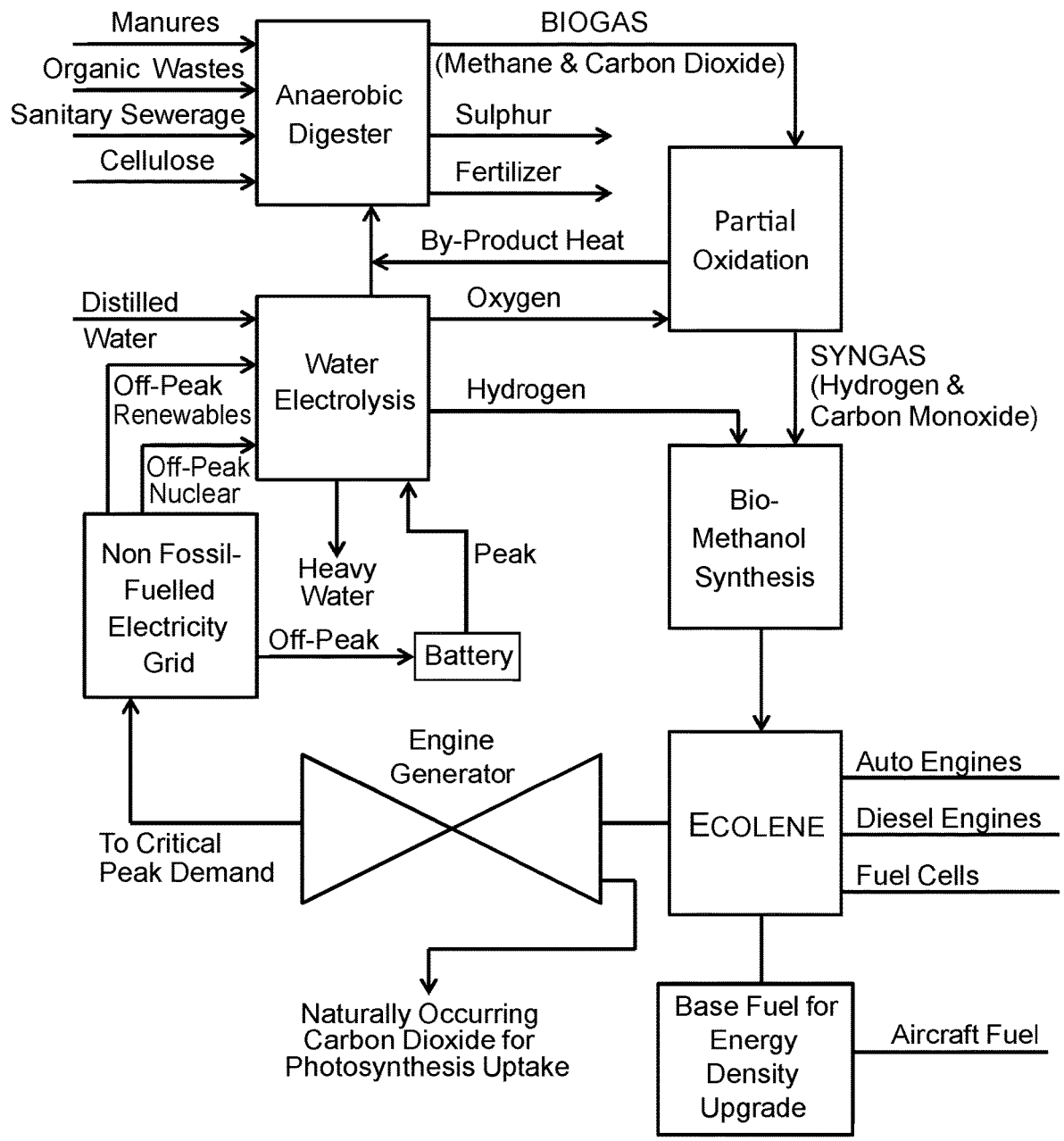
FIG. 2 is a block diagram of an integrated bio-methanol production process with greenhouse gas neutrality.

Referring to FIG. 2, the system can include integrated units for bio-methanol production and can include an anaerobic digester unit, a partial oxidation unit, a synthesis unit, a storage facility, a water electrolysis unit, a battery including associated equipment, and an optional modulating electricity generator.

Figure 3:
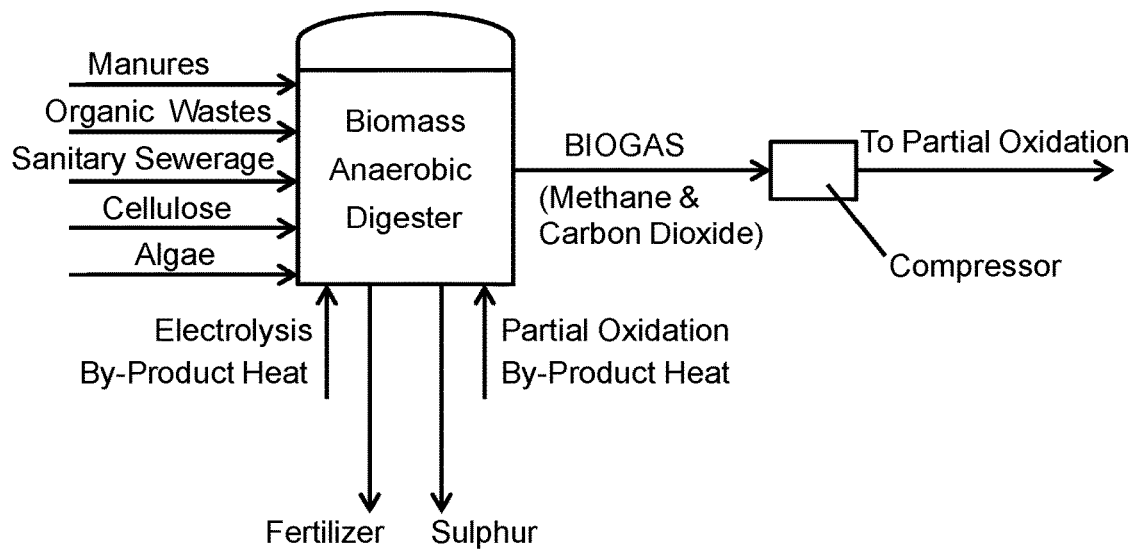
FIG. 3 is a block diagram of a biomass anaerobic digester.

Referring to FIGS. 2 and 3, in some implementations the anaerobic digester is configured to receive one or more biomass feedstocks, such as manures, organic wastes, sanitary sewerage, cellulose (e.g., pulverized cellulose), algae and/or extracts or fractions thereof, and so on. The biomass feedstocks can be sourced locally and can include a combination of different hydrocarbon and carbohydrate sources, and also including algae and/or extracts thereof for example. The digester can be operated to produce biogas as well as sulphur and fertilizer by-product streams. The sulphur can be harvested incrementally and the composted fertilizer can also be recovered periodically, as by-products. The fertilizer can be recovered as a coliform-free material and can be processed for sale and/or used in a dedicated biomass production facility (e.g., a greenhouse) that may also use $CO_2$ that is produced by the process. Both the fertilizer and the $CO_2$ generated by the process can be stored and then supplied as needed to a biomass production facility (e.g., during certain biomass production cycles). In some cases, the biomass that is produced can then be harvested as part of the feedstock supplied to the anaerobic digester. A biogas storage unit can be provided to receive and store biogas from the digester. A biogas compressor can be provided to operate the digester at or near steady state in order to prevent exhausting and/or flaring of biogas during surplus biogas production periods and other times of the processing. The biogas storage can be monitored and controlled to retrieve and supply controlled amounts of the biogas to the partial oxidation unit, for example. Such control can also incorporate input from other process units. The biogas production can be monitored and controlled to obtain a composition within a pre-determined range, particularly with respect to the stoichiometric balance of methane and carbon dioxide, for example to maximize production and utilization.

In some implementations, biogas can be burned directly in the generator, for example in periods of biogas overproduction and/or during outages of partial oxidation and/or synthesis reactors to avoid emissions. The generator unit can include combustion generator devices that are adapted to receive biogas and/or bio-methanol streams as fuel (alternately and/or simultaneously), and/or the generator unit can include multiple generator devices each dedicated to a given fuel (e.g., a biogas-receiving generator, a bio-methanol-receiving generator, etc.).

Figure 4:
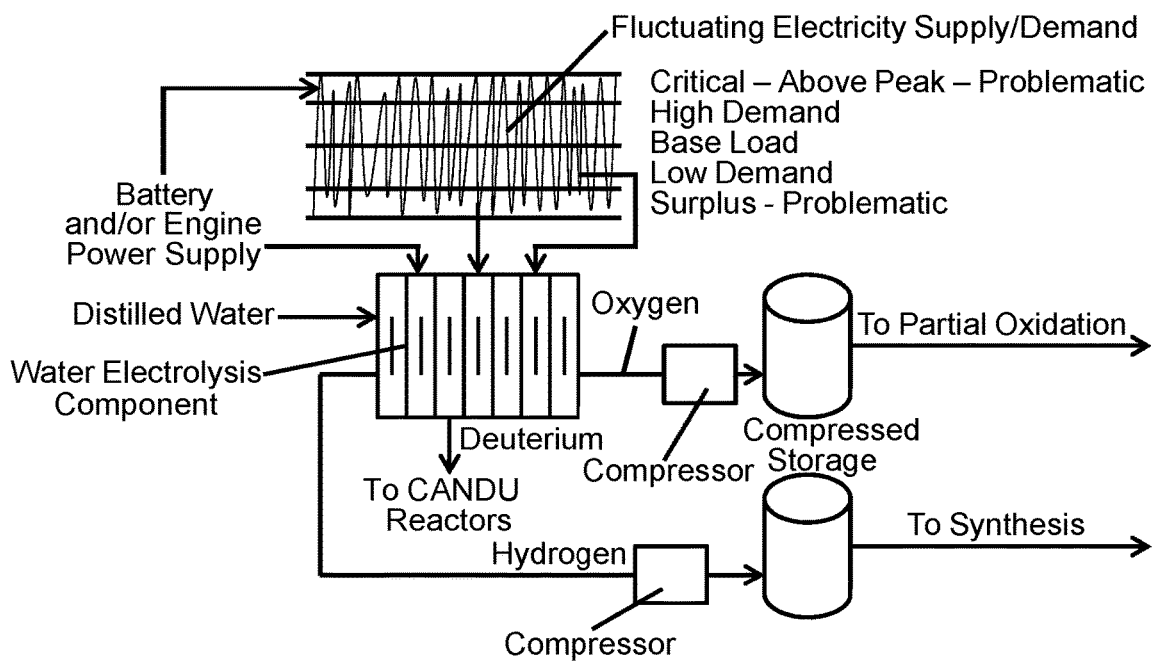
FIG. 4 is a block diagram of a water electrolysis unit operation.

Referring to FIGS. 2 and 4, in some implementations the water electrolysis unit is configured to receive distilled water and electricity from non-fossil fuel sources. The water can be obtained from a water distillation unit or another type of water purification unit that may be located on site or proximate to the water electrolysis unit, for example. Energy required for water distillation can be obtained in whole or in part from renewable sources, such as biomass or bio-methanol combustion. The water electrolysis unit can be fully variable, fully interruptible and outfitted with compressors and storage vessels to ensure a constant regulated supply of output (oxygen and hydrogen) are available during interruption and/or high electricity demand periods. By-product heat from the water electrolysis unit can be captured and delivered to the digester and/or to pre-treatment units for pre-treating the biomass prior to entering the digester. The by-product heat recovery can facilitate temperature control of the digester for optimizing microbial production when appropriate. The by-product heat can be supplied to cooling fans or towers when the heat is not required elsewhere in the process. In addition, the water electrolysis unit can include deuterium harvesting capability, for recovering deuterium (heavy water) for use as a heat transfer medium and/or in medical applications. The water electrolysis unit can thus be configured and operated to promote production of deuterium-rich liquid. For example, the water electrolysis unit can include a cascade of electrolysis chambers for concentrating the deuterium in each subsequent chamber until pure deuterium is produced, or there may be a separate deuterium harvester/separator that is coupled to the water electrolysis unit to receive deuterium-enriched liquid that can be further separated into a substantially pure deuterium via chemical exchange and/or distillation methods. The electrolysis-derived heavy water can be used in a nuclear reactor heat transfer system (e.g., part of a CANDU™ facility).

Figure 5:
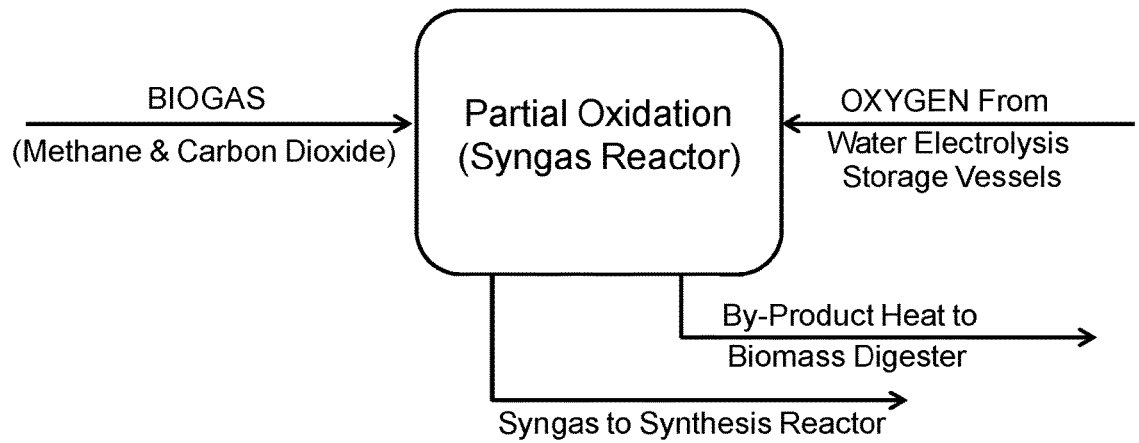
FIG. 5 is a block diagram of a partial oxidation unit.

Referring to FIGS. 2 and 5, in some implementations the partial oxidation unit is fluidly connected with the biogas storage facility and/or the digester, to receive biogas to be burned using compressed oxygen sourced from the water electrolysis unit to produce syngas comprising or substantially consisting of hydrogen and carbon monoxide.

Figure 6:
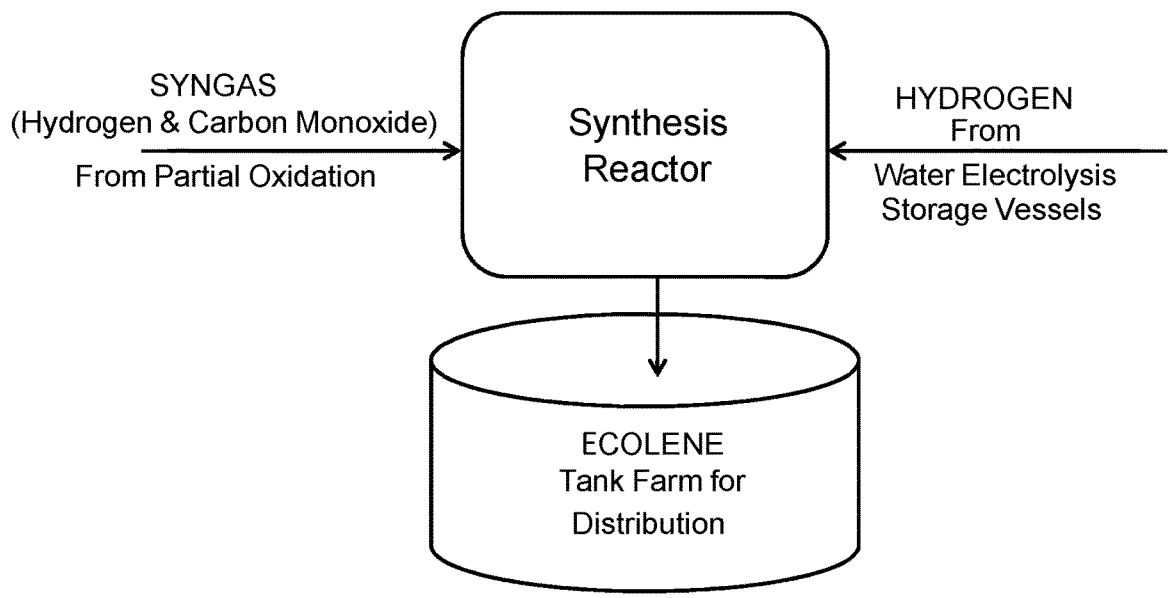
FIG. 6 is a block diagram of a synthesis unit and tank farm.

Referring to FIGS. 2 and 6, in some implementations the syngas together with compressed hydrogen from water electrolysis are supplied to a synthesis unit configured to produce non fossil fuel-based bio-methanol, which may be referred to herein as ECOLENE®.

Still referring to FIGS. 2, 6 and 7, the bio-methanol can be supplied to a storage facility, e.g., tank farm, which can be monitored and controlled in various ways that will be described herein. In some implementations, the bio-methanol storage facility can be configured for distribution as well as periodic supply to a generator for electricity generation. In some implementations, the bio-methanol storage facility is configured with sufficient tank storage inventory or capacity to enable periodic electricity generation, for example during critical peak demand. The tank storage capacity can therefore be coordinated with electrolysis electricity demand and peak non fossil fueled electricity demand. The storage facility can also include piping, monitoring instrumentation, pumps and control units to manage the storage and the supply of the bio-methanol.

In some implementations, the capacity to intermittently utilize surplus and/or low demand electricity in variable amounts to produce non fossil-sourced hydrocarbons with the capacity to intermittently generate critical and high demand electricity in variable amounts can facilitate the increasing need to balance electricity supply with electricity demand. The capacity to produce bio-methanol during low electricity demand and use the bio-methanol and/or battery power to provide electricity during high electricity demand can help reduce demand charges and improve the quality of electricity. In some scenarios, time-of-day pricing by electricity system operators can be used to determine the value for using surplus electricity capacity for purchasing low demand electricity and a charge for demand. The capacity to generate electricity using bio-methanol ECOLENE® and/or biogas can be determined by the steady state capacity of the biogas using ECOLENE® as a back-up biofuel. For example, a 20,000 US gal/day "regional" bio-methanol plant may use 75,000 $m^3$ biogas/day, which is generally reflected in FIG. 8.

Time-of-use pricing of electricity can vary depending on various factors and locations. For example, in some jurisdictions, off-peak electricity rates can apply from approximately 8:00 PM-7:00 AM and can have a cost that is about 65-75% of the mid-peak rate and about 30-55% of the on-peak rate.

In some implementations, the capacities of the different units can be coordinated with factors based on electricity demand cycles, estimated fuel market, and the like. In some scenarios, the digester is sized and operated to produce between 25,000 $m^3$/day and 200,000 $m^3$/day biogas, or between 50,000 $m^3$/day and 100,000 $m^3$/day biogas; the bio-methanol synthesis unit is sized and operated to produce between 5,000 gal/day and 100,000 gal/day of bio-methanol, or between 15,000 gal/day and 25,000 gal/day; and the bio-methanol storage facility has a capacity of between 15,000 gallons and 100,000 gallons, or between 40,000 gallons and 80,000 gallons of the biofuel. Subject to biomass availability, much larger bio-methanol plants can be implemented in the proximity of large nuclear and/or renewable electricity generating sites.

Figure 7:
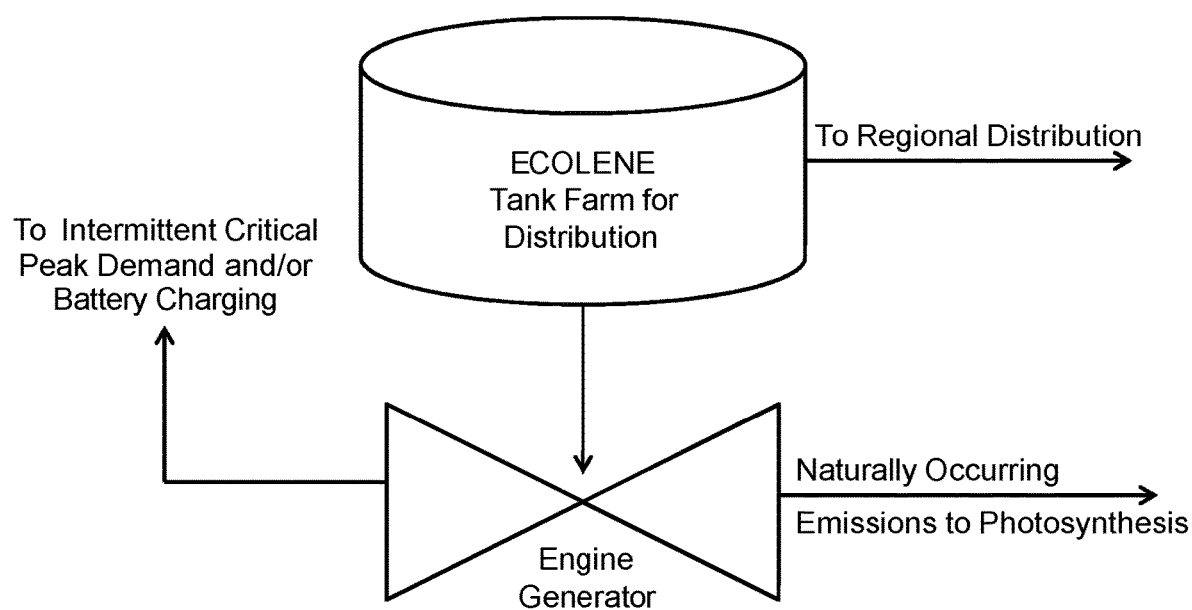
FIG. 7 is a block diagram of a generator.
Figure 8:
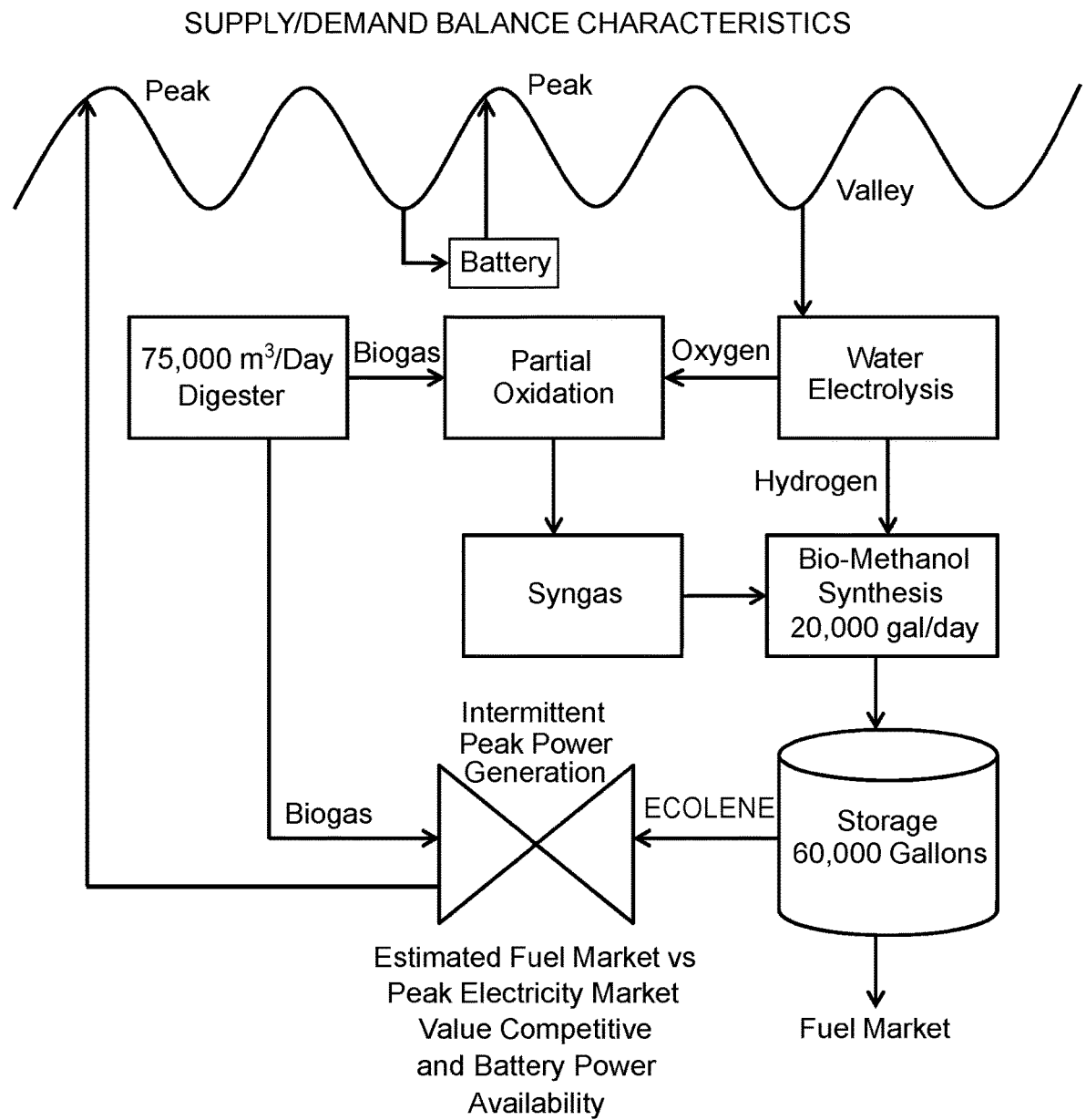
FIG. 8 is a block diagram of several integrated units and illustrating the electricity source in terms of its supply-demand balance characteristics.

Referring to FIG. 7, a generator can be provided to receive bio-methanol from the storage facility and provide electricity to the water electrolysis unit. The generator may be specially designed and dedicated for the combustion of bio-methanol to produce electricity without emitting fossil fuel sourced greenhouse gases. The generator can be configured to receive different fuels, which may be liquid non fossil-sourced fuels only or a combination of liquid non fossil-sourced fuels including biogas. The combustion of the bio-methanol and/or biogas would be substantially free of fossil sourced greenhouse gas emissions that would be associated with the combustion of fossil fuels, for example. By-product heat from the generator can also be used in the process, e.g., for optimizing the microbial production in the digester.

An integration assembly can be provided to integrate different units of the system. For example, the integration assembly can include the generator, inlet bio-methanol fuel piping, electrical supply lines for supplying bio-methanol generated electricity to the water electrolysis unit, a control unit coupled to the piping and/or valves for controlling the periodic operation of the generator, which may be done according to input variables that include electricity demand levels to determine the timing of peak demand, as well as various detection and monitoring devices such as temperature sensors, pressure sensors and/or flow rate meters and/or actuators. The integration assembly may include an automation apparatus, such as a computer, configured to control the integration automatically in response to the input variables to ensure pressure/temperature and processing duration for the conversion process (e.g., space, gas, velocity). The integration assembly can also be connected to the battery and its associated equipment.

Various techniques described herein can be used in the context of a carbon capture, carbon storage, carbon trade, carbon credit, and carbon tax systems.

Production of ECOLENE® can enable a liquid hydrocarbon to be commercially synthesized by controlled digestion of waste biomass as feedstock to capture and utilize methane and carbon dioxide to produce a biofuel rather than enter the atmosphere directly as greenhouse gases. By utilizing only renewable- and/or nuclear-sourced electricity, to decompose water to produce the essential elements of hydrogen and oxygen, unlike other methanol synthesis processes which use fossil fuel-sourced input streams, ECOLENE® production enables its emissions of carbon dioxide to remain more in atmospheric balance through photosynthesis.

In some implementations, the system can be a regional hub that is located to serve a remote solar farm, a remote hydraulic generation facility, a remote wind farm and/or an ocean energy facility where conventional grids or related infrastructure are inadequate or do not exist. Bio-methanol can thus be a particularly advantageous source of electricity storage and/or a liquid carrier/transporter of electron energy. Batteries can also be advantageous in terms of accumulating and storing energy for stable operation of the bio-methanol production process.

In some implementations, the bio-methanol can also be used as a liquid fuel for various conventional and/or hybrid transportation power trains, as well as other methods. Thus, using biomass, water and variable volumes of renewable and/or nuclear sourced electricity during low electricity system demand, as described herein, can enable bio-methanol to be used to power internal combustion engines for conventional power trains, on-board generators for hybrid and/or all electric power trains, carry hydrogen for fuel cell powered electric drives and/or generate electricity during high electricity demand, qualifying such bio-methanol to be a liquid electricity storage medium "battery" (N.B., to be distinguished from the electrical battery disclosed herein). Bio-methanol production, storage inventory and distribution can be managed to facilitate a plurality of end-uses that can be coordinated with advantageous time periods (e.g., electricity demand cycles), locations (e.g., regional, infrastructure-deficient, etc.), as well as various cost/economic factors. In some implementations, the bio-methanol can also be used to charge one or more of the batteries, for example during peak demand periods and/or when bio-methanol inventory is high or near capacity of the tank farm.

Figure 9:
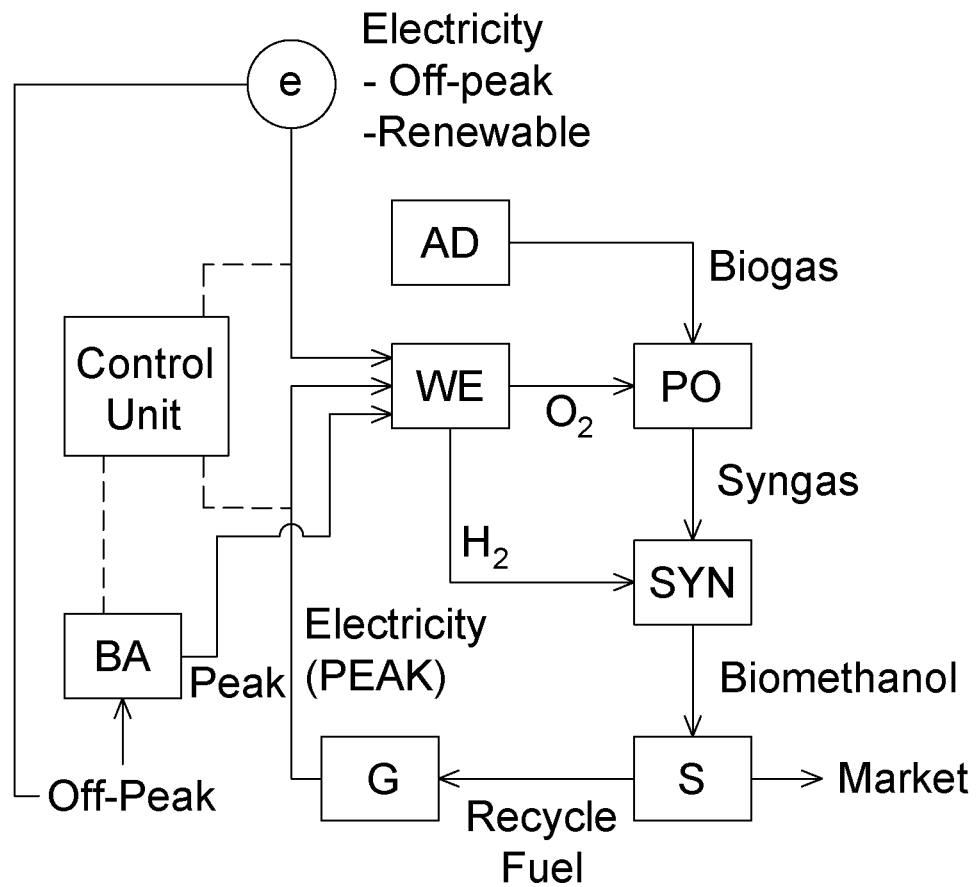
FIG. 9 is another block diagram of an integrated bio-methanol production process.

Referring to FIG. 9, the overall bio-methanol fuel production process is illustrated where a control unit is coupled to both the electrical output of the generator (G), the battery (BA), and an electrical line from an external electricity source (e), which may include electricity from an electricity grid dominated with renewable sources to ensure the electricity flow is carbon neutral. The control unit can be configured to receive information regarding the bio-methanol production process as well as the external electricity/power source(s), including cost information for external electricity as well as for inputs (e.g., biomass feedstocks) and outputs (e.g., bio-methanol) of the production system. The control unit can be configured to balance the electricity sources (i.e., internal and external) to minimize cost or to reduce cost while prioritizing more sustainable electricity sources. The control unit can also be configured to use a certain electricity source in the event of an outage or maintenance of one of the other sources (e.g., batteries can be prioritized when one or more generator is off-line).

Figure 10:
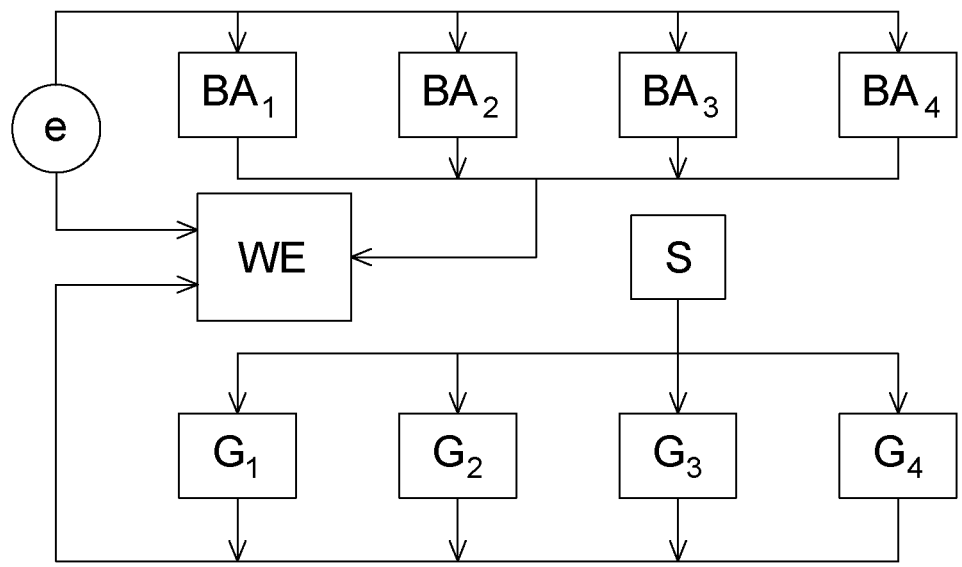
FIG. 10 is a block diagram of part of a bio-methanol production process.

Referring to FIG. 10, a water electrolysis unit (WE) can receive electricity from external sources (e), internal generator sources ($G_1$ to $G_n$) and battery sources ($BA_1$ to $BA_n$). In some scenarios, it may be advantageous to provide multiple generators ($G_1$ to $G_n$) and/or multiple batteries (BA) which can be operated individually or together depending on the electricity demand from the water electrolysis unit (WE). For example, during high throughput/production periods and peak demand, multiple or all of the generators and/or batteries can be operated to provide electricity; while during lower throughput/production periods and/or off-peak, only some or none of the generators and/or batteries can be operated to provide electricity. Multiple smaller generators and/or batteries, all of which can be coupled to a central control unit, can thus be used in a modular fashion to tailor the electricity generation in a flexible manner that can adapt to both external electricity cost and availability and the production mode (e.g., high production, start-up, turndown, upset, etc.) of the bio-methanol production process.

Figure 11:
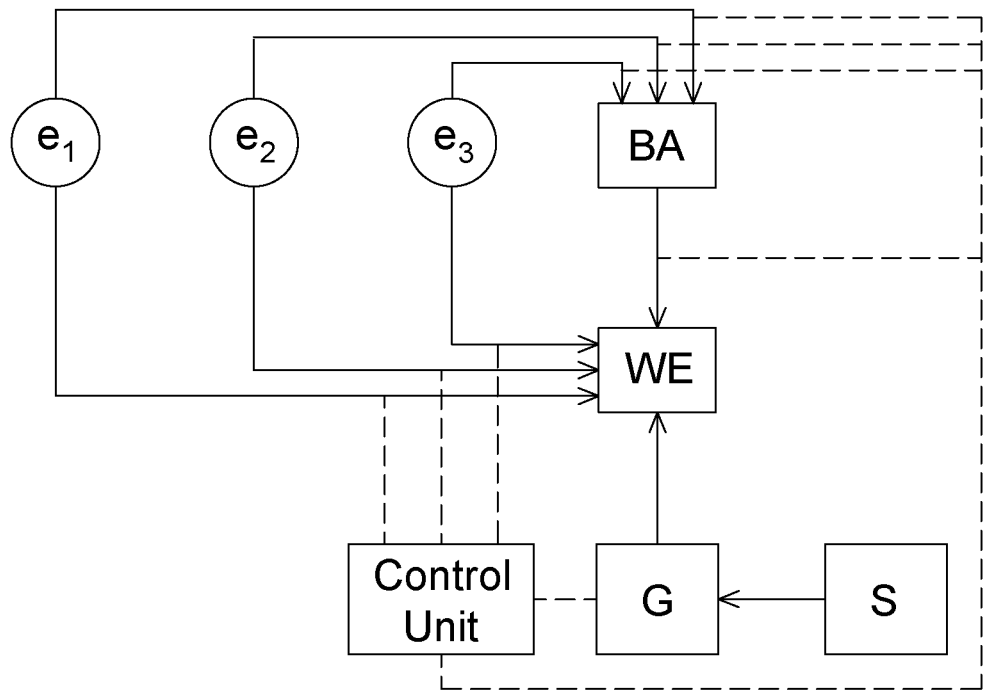
FIG. 11 is another block diagram of part of a bio-methanol production process.

Referring to FIG. 11, the water electrolysis unit (WE) can be coupled to multiple external electricity sources ($e_1$ to $e_3$), each of which can originate from a different electricity generation method. For example, a first external electricity source ($e_1$) may be wind-generated, a second external electricity source ($e_2$) may be hydro-generated, a third external electricity source ($e_3$) may be nuclear-generated, while other external electricity sources may come from various other renewable sources, some of which have been mentioned above. By coupling the bio-methanol production process to multiple external electricity sources, access to renewable electricity can be more robust particularly when some of the output from the renewable sources is inconsistent or difficult to predict in terms of availability and/or cost. For example, certain renewable energy sources are weather dependent (e.g., wind) and thus by providing multiple external sources, the process can operate more efficiently. In addition, the control unit can be configured to select and balance the electricity sources that are used for the water electrolysis unit based on fluctuations in each external electricity source.

Figure 12:
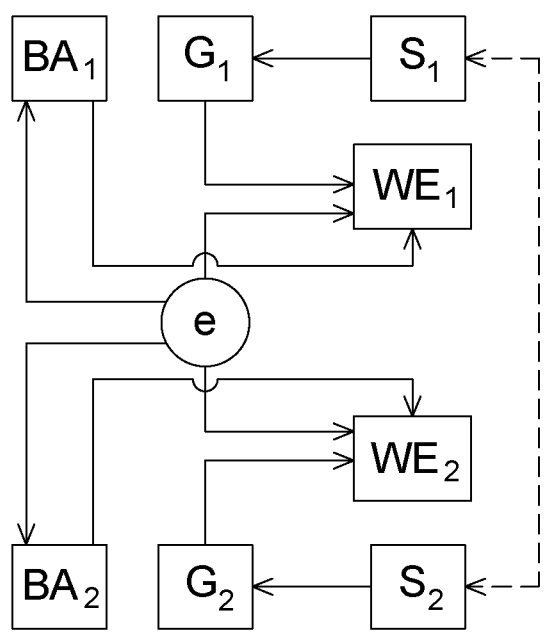
FIG. 12 is another block diagram of part of a bio-methanol production process.

Referring to FIG. 12, multiple water electrolysis units can be provided and in some cases can employ one or more common external electricity source (e). The multiple water electrolysis units can be part of the same overall bio-methanol production process or they can be part of two distinct and potentially remote processes, e.g., provided in two different regional locations. Each water electrolysis unit ($WE_1$ and $WE_2$) can be coupled to its own generator ($G_1$ and $G_2$ respectively) and/or battery ($BA_1$ and $BA_2$ respectively), where the generators can in turn be coupled to two different storage facilities ($S_1$ and $S_2$ respectively) or to a single central storage facility. This general configuration can be particularly advantageous for implementing multiple bio-methanol production plants in a plurality of remote locations that are nevertheless serviced by a common electrical grid and/or by common external electrical sources. In addition, a bank of generators can include a primary generator as well as backup generators, which can come online quickly and periodically to facilitate avoiding spikes in peak demand. There may also be a bank of batteries with a primary battery as well as backup batteries, which can come online quickly and periodically to facilitate avoiding spikes in peak demand. There may alternatively be a primary battery or generator, and at least one backup of the other type of electricity source (generator or battery). Multiple generators and/or batteries can thus be particularly advantageous when there are sudden, large and/or unpredictable spikes in peak demand, by facilitating rapid adjustment.

In some implementations, the primary generator ($G_1$) or battery ($BA_1$) can be designed and provided to be able to respond to normal electricity requirements during peak demand periods and typical operation of the bio-methanol production plant, while a secondary or backup generator ($G_2$) or battery ($BA_2$) is a smaller unit designed for more occasional operation during sudden peaks, emergency demand periods, and/or when bio-methanol price is lower than external electricity cost. In some implementations, one or more generators can be designed to utilize the bio-methanol as the dedicated fuel, while one or more additional generators are provided for use with other fuel sources (e.g., biogas) or as fuel-neutral units that can receive methanol, biogas and/or other fuel sources for electricity generation.

Figure 13:
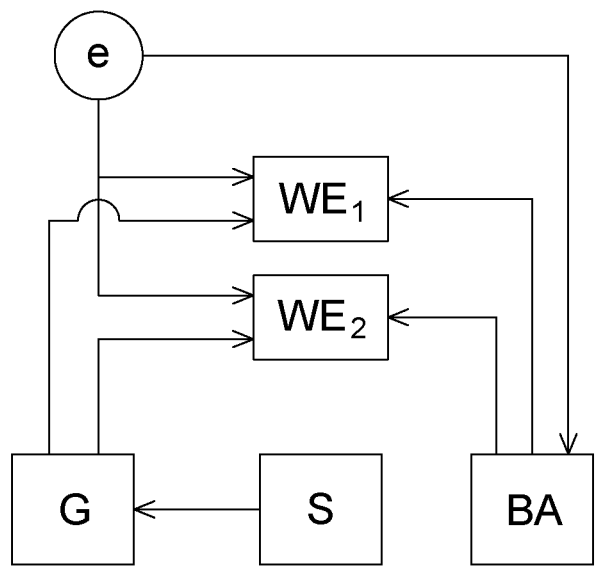
FIG. 13 is another block diagram of part of a bio-methanol production process.

Referring to FIG. 13, the bio-methanol production process can include multiple water electrolysis units ($WE_1$ and $WE_2$) that are part of the same production plant and are operated in accordance with electricity sourcing strategy and the bio-methanol production mode. For example, during low throughput/production (e.g. during start-up or turndown modes, maintenance, or feedstock modification) a single water electrolysis unit may be used and it may be supplied with electricity based on the above-described methods by using off-peak electricity from the external source (e), and bio-methanol generated electricity or battery power during peak periods. As the production process ramps up, the second water electrolysis unit can come online and can be supplied by both external and internal sources of electricity (generator and/or battery), as described above. A bank of multiple water electrolysis units can provide additional flexibility for bio-methanol production processes, particularly when the plants have variable throughputs and production.

In addition, the production rate of the process can also be controlled based on electricity availability and cost. For example, during peak demand, the production rate can be decreased in conjunction with using bio-methanol to generate electricity for operating the water electrolysis unit(s) or using battery power. This can be particularly advantageous in the case that the bio-methanol market price is high and/or when the biomass feedstock cost is high, thereby reducing the consumption of bio-methanol for generating electricity while keeping the process operational during peak demand periods. Alternatively, when bio-methanol price and feedstock cost are low, the production rate can be maintained at substantially the same levels as during off-peak operations.

Figure 14:
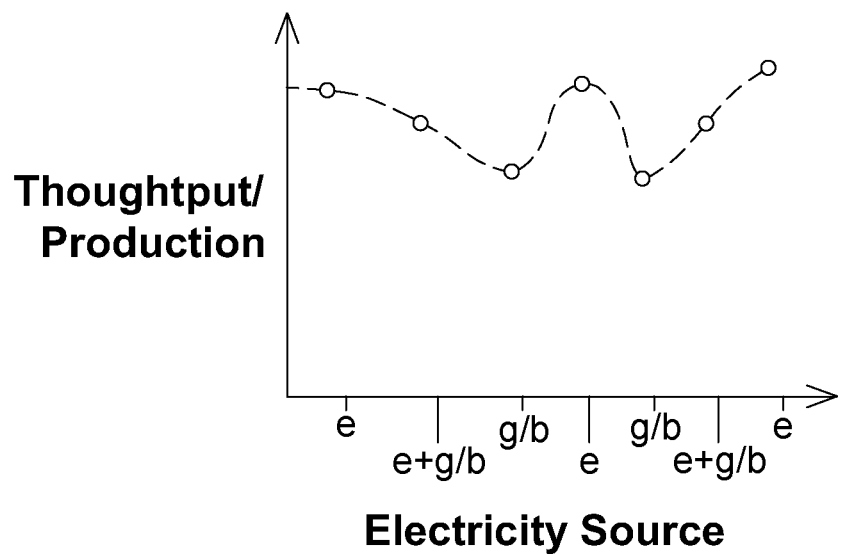
FIG. 14 is a graph of throughput/production versus electricity source for an example bio-methanol production process.

Turning to FIG. 14, an example of modulating throughput and production rate of the process based on the different electricity inputs (e), (G) and (b) is illustrated. One can also integrate the cost of biomass feedstocks, the price of the bio-methanol, and capital/operating costs of the battery units, into the control strategy which can be implemented in automated fashion by a control unit that is coupled to the various units of the process.

Advantageously, off-peak external electricity consists of electricity from non-fossil fuel sources. Various examples of non-fossil fuel sources of electricity are provided further above. Further examples are (i) when nuclear reactors are modulated or when primary nuclear sourced steam is being quenched, (ii) when wind energy generation is being strategically curtailed, (iii) when hydro-energy is being spilled as part of a supply management strategy. A number of variable electricity sources can be used.

In addition, since water electrolysis units can incrementally and quickly modulate demand, utilizing water electrolysis units in the context of the techniques described herein facilitates critical load manipulation. Electrolysis interruption is ideally avoided and thus leveraging the battery stored energy and/or the bio-methanol for providing electricity dedicated for maintaining electrolysis operation facilitates efficient operation of the process.

In some implementations, the generator (G) is a dedicated bio-methanol combustion unit that is designed and operated for use with 100% methanol as fuel. Alternatively, the generator can be used for various different fuel types, including methanol. In some implementations, the combustion gas generated by the generator(s) is recuperated and reused either within the bio-methanol production process or in other processes. For instance, in some scenarios, the $CO_2$ in the combustion gas can be separated and reused in the process, in another system (e.g., greenhouses for photosynthesis and production of biomass including cultured algae as an example), and/or in a capture/sequestration system. The $CO_2$ in the combustion gas can be prepared and supplied directly to a $CO_2$-utilization facility or can be captured from the combustion gas and stored as substantially pure $CO_2$ for use. Heat generated by the generator can also be used in a biomass generation facility, such as a greenhouse, or other external or internal units. In some scenarios, at least one of the generators can be portable to facilitate relocation as need be, e.g., between two remote process locations.

In some implementations, the one or more batteries can be charged using one or more sources. For example, the battery can be charged using off-peak electricity from the grid, other energy sources as mentioned above, combustion of bio-methanol, and/or combustion of other fuels that are non-fossil fuels (e.g. biomass based). The battery charging approach can be based on various strategies, and can prioritize various energy sources based on availability, sustainability, cost, availability of other energy sources at different times (e.g., peak versus off-peak), electrolysis electricity demand, and so on.

It is noted that aspects of this integrated process technology can be described as an including the transformation of idled electricity from electrons to molecules via water electrolysis. The integration of water electrolysis, as described herein, facilitates energy in the form of electrons/ electricity to become energy in the form of molecules.

Units and components of the systems described herein can also be used and configured in various ways. For example, certain unit operations can be provided as a serial or parallel bank of units. Another example is that processes described herein can be adapted for production of liquid biofuel other than bio-methanol by periodically using liquid biofuel as a source of electricity for one or more units during peak demand periods, particularly when such electricity is supplied to a water electrolysis unit or another unit having similar electricity requirements. In addition, multiple generators and/or batteries can be provided in parallel, the generators being able to process different amounts of bio-methanol to produce electricity for the water electrolysis unit depending on the electricity demand, the electrolysis electricity demand and/or the inventory of bio-methanol.

The invention claimed is:

1. A method for producing bio-methanol, comprising:
supplying biomass to an anaerobic digester for producing biogas comprising methane and carbon dioxide;
supplying the biogas and oxygen sourced from water to a partial oxidation unit to produce syngas;
supplying the syngas with hydrogen sourced from water to a synthesis unit and producing the bio-methanol;
supplying distilled water to a water electrolysis unit to produce electrolysis oxygen and electrolysis hydrogen;
supplying at least a portion of the electrolysis hydrogen as at least part of the hydrogen used in the synthesis unit;
supplying at least a portion of the electrolysis oxygen as at least part of the oxygen used in the partial oxidation unit; and
powering the electrolysis unit using different sources of energy, wherein:
during electricity demand of an electrical grid below a base threshold, the electrolysis unit is powered using energy from the electrical grid and a battery is charged from the electrical grid, and
during electricity demand of the electrical grid over a base threshold, the electrolysis unit is powered at least in part using energy stored in the battery.

2. The method of claim 1, wherein the biomass comprises manure, organic waste, sewerage, cellulose and/or algae.

3. The method of claim 1, wherein the anaerobic digester further produces sulphur and/or organic fertilizer.

4. The method of claim 1, further comprising heating the anaerobic digester using by-product heat generated by the partial oxidation unit.

5. The method of claim 1, further comprising heating the anaerobic digester using by-product heat generated by the water electrolysis unit.

6. The method of claim 1, wherein an oxygen feed supplied to the partial oxidation unit consists of the electrolysis oxygen.

7. The method of claim 1, wherein the oxygen supplied to the partial oxidation unit is obtained from an oxygen storage vessel.

8. The method of claim 1, wherein a syngas feed supplied to the synthesis unit consists of the syngas produced by the partial oxidation unit.

9. The method of claim 1, wherein a hydrogen feed supplied to the synthesis unit consists of the electrolysis hydrogen.

10. The method of claim 1, wherein the water electrolysis unit further produces deuterium.

11. The method of claim 10, wherein at least a portion of the deuterium is supplied to a nuclear reactor facility.

12. The method of claim 1, wherein:
during electricity demand of the electrical grid over an upper value:
powering the water electrolysis unit in part using electricity obtained from a generator fueled with a portion of stored bio-methanol that has been stored in a storage vessel; and
during electricity demand of the electrical grid below a lower value:
powering the water electrolysis unit using electricity obtained from a source supplied by renewable and/or nuclear energy sources and/or from independent renewable electricity generators.

13. The method of claim 1, wherein the base threshold is relatively constant and pre-determined.

14. The method of claim 1, wherein the upper and lower values are the same.

15. The method of claim 14, wherein the upper and lower values and the base threshold are the same.

16. The method of claim 1, wherein the biomass comprises cellulose.

17. The method of claim 1, further comprising controlling electricity input into the water electrolysis unit and controlling the electricity generation from the bio-methanol to maintain overall greenhouse gas neutrality of the process.

18. The method of claim 1, wherein the electrical grid used to power the electrolysis unit periodically provides electricity that is exclusively derived from renewable or nuclear sources or a combination thereof.

19. A system for producing bio-methanol, comprising:
an anaerobic digester unit for producing biogas comprising methane and carbon dioxide;
a partial oxidation unit for receiving the biogas and configured to produce syngas;
a synthesis unit for receiving the syngas and hydrogen, and configured to produce bio-methanol;
a water electrolysis unit to produce oxygen and hydrogen;
a power control assembly configured to:
supply power from a battery to the water electrolysis unit, during critical electricity demand of an external electrical system over an upper threshold, and
supply power from a second power source to the water electrolysis and not from the battery, during electricity demand of an external electrical system below a lower threshold;
a hydrogen supply and storage assembly configured to supply at least a portion of the electrolysis hydrogen as at least part of the hydrogen used in the synthesis unit; and
an oxygen supply and storage assembly configured to supply at least a portion of the electrolysis oxygen as at least part of the oxygen used in the partial oxidation unit.

20. A method for producing bio-methanol, comprising:
supplying biomass to an anaerobic digester for producing biogas comprising methane and carbon dioxide;
supplying biogas and oxygen to a partial oxidation unit to produce syngas;
supplying syngas and hydrogen to a synthesis unit and thereby producing the bio-methanol;
supplying water to a water electrolysis unit to produce electrolysis oxygen and electrolysis hydrogen;
supplying at least a portion of the electrolysis hydrogen as at least part of the hydrogen used in the synthesis unit;
supplying at least a portion of the electrolysis oxygen as at least part of the oxygen used in the partial oxidation unit; and
integrating bio-methanol storage, electricity generation and electrolysis, comprising:
storing an inventory of bio-methanol, and controlling electricity input into the water electrolysis unit, comprising:
    monitoring electricity demand of an external electrical system, and
    based on the monitored electricity demand of the external electrical system, periodically:
        combusting a portion of the bio-methanol retrieved from the inventory to provide bio-methanol-generated electricity,
        utilizing the bio-methanol-generated electricity in the water electrolysis unit, and
        powering the water electrolysis unit in part using electricity obtained from a pre-charged battery.

* * * * *